United States Patent
Chiyomaru et al.

(10) Patent No.: US 12,360,127 B2
(45) Date of Patent: Jul. 15, 2025

(54) CONCENTRATION MONITORING SYSTEM, CONCENTRATION MANAGEMENT SYSTEM, AND CONCENTRATION MONITORING METHOD

(71) Applicant: MITSUBISHI HEAVY INDUSTRIES, LTD., Tokyo (JP)

(72) Inventors: Masaru Chiyomaru, Tokyo (JP); Hiroaki Mikawa, Tokyo (JP); Yuichi Okuzaki, Tokyo (JP)

(73) Assignee: MITSUBISHI HEAVY INDUSTRIES, LTD., Tokyo (JP)

( * ) Notice: Subject to any disclaimer, the term of this patent is extended or adjusted under 35 U.S.C. 154(b) by 490 days.

(21) Appl. No.: 17/631,041

(22) PCT Filed: Aug. 4, 2020

(86) PCT No.: PCT/JP2020/029886
§ 371 (c)(1),
(2) Date: Jan. 28, 2022

(87) PCT Pub. No.: WO2021/059754
PCT Pub. Date: Apr. 1, 2021

(65) Prior Publication Data
US 2022/0268752 A1      Aug. 25, 2022

(30) Foreign Application Priority Data
Sep. 26, 2019  (JP) .................. 2019-174990

(51) Int. Cl.
*G01N 35/00*  (2006.01)
(52) U.S. Cl.
CPC . *G01N 35/00623* (2013.01); *G01N 35/00663* (2013.01); *G01N 35/00693* (2013.01); *G01N 2035/00673* (2013.01)

(58) Field of Classification Search
CPC ................... G01N 35/00693; G01N 35/00623
See application file for complete search history.

(56) References Cited

U.S. PATENT DOCUMENTS

| | | | |
|---|---|---|---|
| 5,639,954 A | * | 6/1997 | Crothers ................ B23K 1/203 73/1.01 |
| 6,255,123 B1 | | 7/2001 | Reis |

(Continued)

FOREIGN PATENT DOCUMENTS

| | | |
|---|---|---|
| JP | 60004842 A | 1/1985 |
| JP | 60021443 A | 2/1985 |

(Continued)

OTHER PUBLICATIONS

International Search Report and Written Opinion of International Application No. PCT/JP2020/029886 mailed Oct. 20, 2020; 14pp.

*Primary Examiner* — Nathaniel J Kolb
(74) *Attorney, Agent, or Firm* — HAUPTMAN HAM, LLP

(57) ABSTRACT

Provided is a concentration monitoring system which allows continuous concentration monitoring of a processing tank. The concentration monitoring system is provided with a first cycle in which a sample of a processing liquid to which a chemical has been added is taken from a processing tank in which the processing liquid is stored and supplied to a concentration meter which measures the concentration of the chemical, a second cycle in which a chemical solution having a known concentration of the chemical is supplied to the concentration meter, and a control device which controls the first cycle to evaluate the concentration of the chemical in the processing tank on the basis of the concentration of the sample measured by the concentration meter and controls the second cycle to evaluate the precision of the concentra- (Continued)

tion meter on the basis of the concentration of the chemical solution measured by the concentration meter.

7 Claims, 6 Drawing Sheets

(56) References Cited

U.S. PATENT DOCUMENTS

| | | | |
|---|---|---|---|
| 2003/0015417 | A1 | 1/2003 | Fulton et al. |
| 2003/0049169 | A1 | 3/2003 | Chiba et al. |
| 2011/0244578 | A1* | 10/2011 | Rajagopalan ...... G01N 33/1846 436/8 |
| 2011/0301917 | A1 | 12/2011 | Kamihara et al. |

FOREIGN PATENT DOCUMENTS

| | | | |
|---|---|---|---|
| JP | 63010233 | B | 3/1988 |
| JP | H07306146 | A | 11/1995 |
| JP | 08178913 | A | 7/1996 |
| JP | 10090275 | A | 4/1998 |
| JP | 2876411 | A | 3/1999 |
| JP | 2876411 | B | 3/1999 |
| JP | 2001324489 | A | 11/2001 |
| JP | 2002047575 | A | 2/2002 |
| JP | 2004534909 | A | 11/2004 |
| JP | 2007187446 | A | 7/2007 |
| JP | 5557750 | B | 7/2014 |
| JP | 2016029208 | A | 3/2016 |

* cited by examiner

CONCENTRATION MONITORING SYSTEM, CONCENTRATION MANAGEMENT SYSTEM, AND CONCENTRATION MONITORING METHOD

RELATED APPLICATIONS

The present application is a National Phase of International Application Number PCT/JP2020/029886 filed Aug. 4, 2020 and claims priority of Japanese Application Number 2019-174990 filed Sep. 26, 2019.

TECHNICAL FIELD

The present disclosure relates to a concentration monitoring system, a concentration management system, and a concentration monitoring method. The present application claims priority based on Japanese Patent Application No. 2019-174990 filed in Japan on Sep. 26, 2019, the contents of which are incorporated herein by reference.

BACKGROUND ART

In a line for performing a surface treatment of aircraft members such as aluminum or titanium, there are treatment steps such as degreasing, washing, etching, and coating. In each treatment step, it is necessary to manage concentration of a chemical in treatment liquid. For example, in a step of forming a film by an anodizing treatment, phosphoric acid concentration in the treatment liquid is manually measured by using a method such as a neutralization titration method or an aluminum analysis method to perform a concentration management.

PTL 1 discloses a method for measuring the concentration of each substance in treatment liquid in a surface washing step of a semiconductor substrate. In the measuring method of PTL 1, a light emitting substance that chemically emits light in response to a specific substance in the treatment liquid is added to the treatment liquid to emit light, and the concentration of the specific substance is measured based on the light emitting lightness.

CITATION LIST

Patent Literature

[PTL 1] Japanese Unexamined Patent Application Publication No. 7-306146

SUMMARY OF INVENTION

Technical Problem

As described above, the phosphoric acid concentration is often measured by using a manual analysis. In order to maintain the phosphoric acid concentration of the treatment liquid within a predetermined range, continuous and consecutive concentration monitoring is required. However, manual concentration measurement takes time, and even when the concentration measurement is performed regularly, continuous monitoring is difficult. The concentration of the treatment liquid in the treatment tank is affected by the number of treatments of a target product, treatment time, and other treatment steps on an upstream-side. For example, when the number of treatments of the product increases rapidly, the concentration of the treatment liquid also changes rapidly. However, the manual concentration measurement may not be able to cope with such changes.

The present disclosure provides a concentration monitoring system, a concentration management system, and a concentration monitoring method that can solve the above problems.

Solution to Problem

According to the present disclosure, there is provided a concentration monitoring system including: a first cycle for collecting a sample of treatment liquid from a treatment tank, which stores the treatment liquid to which a chemical is added, and supplying the sample to a concentration meter which measures concentration of the chemical; a second cycle for supplying a chemical solution having known concentration of the chemical to the concentration meter; and a control device that controls the first cycle to evaluate concentration of the chemical in the treatment tank based on concentration of the sample measured by using the concentration meter, and controls the second cycle to evaluate accuracy of the concentration meter based on concentration of the chemical solution measured by using the concentration meter.

According to the present disclosure, there is provided a concentration management system including: the concentration monitoring system described above; and an automatic addition system that adds the chemical or a diluted solution of the chemical to the treatment tank when the concentration monitoring system evaluates that the concentration in the treatment tank is abnormal.

According to the present disclosure, there is provided a concentration monitoring method including: collecting a sample of treatment liquid from a treatment tank, which stores the treatment liquid to which a chemical is added, supplying the sample to a concentration meter which measures concentration of the chemical, and evaluating concentration of the chemical in the treatment tank; and supplying a chemical solution having known concentration of the chemical to the concentration meter while the sample is not supplied to the concentration meter and evaluating accuracy of the concentration meter based on concentration of the chemical solution measured by using the concentration meter.

Advantageous Effects of Invention

According to the above-mentioned concentration monitoring system, the concentration management system, and the concentration monitoring method, it is possible to consecutively and continuously monitor the concentration in the treatment liquid.

DESCRIPTION OF EMBODIMENTS

Embodiment

Hereinafter, a concentration monitoring system and a concentration management system according to an embodiment will be described with reference to FIGS. 1 to 6.
(System Configuration)

Figure 1:
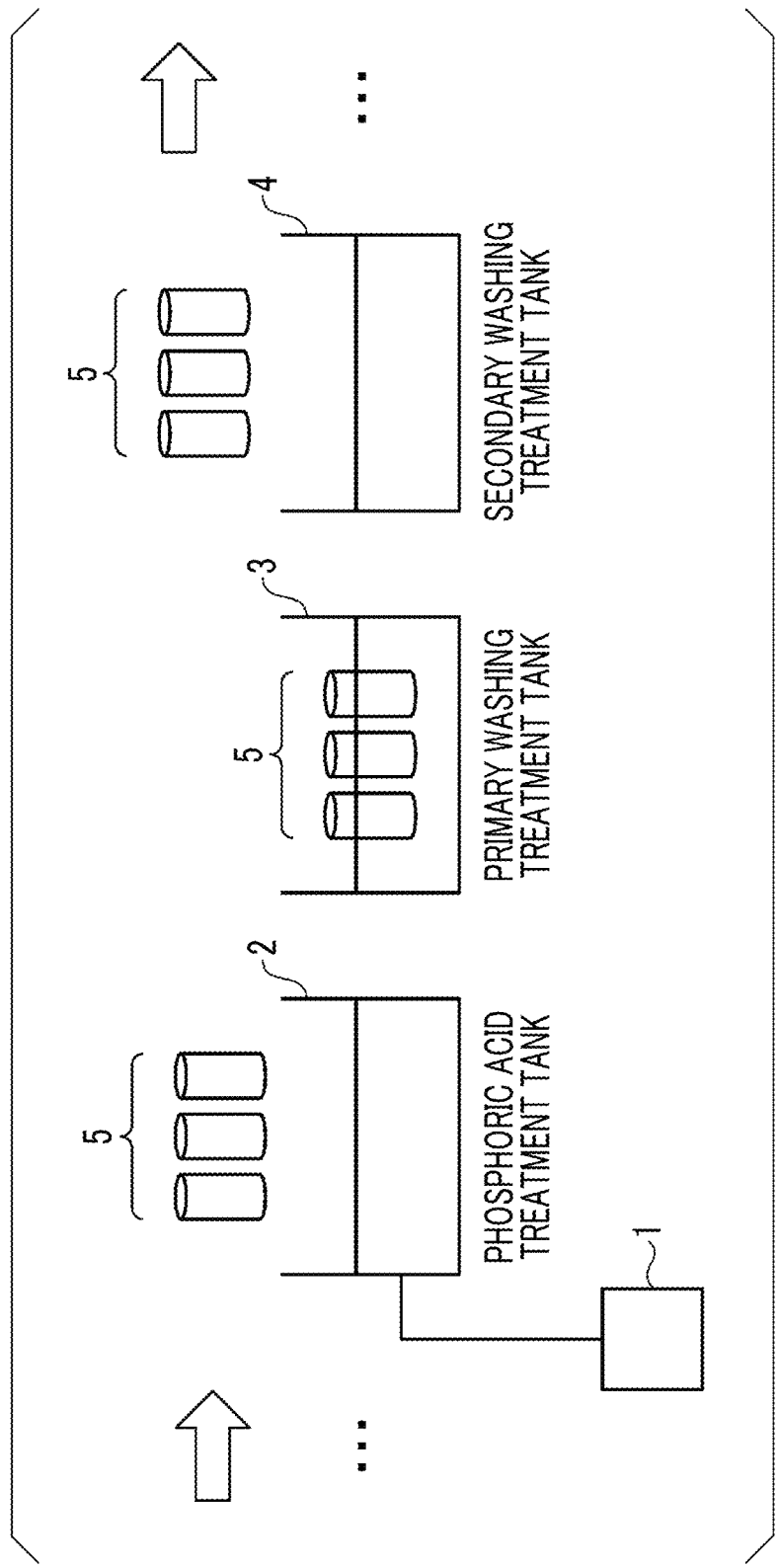
FIG. 1 is a schematic diagram of a surface treatment line including a concentration monitoring system according to an embodiment.

FIG. 1 is a schematic diagram of a surface treatment line including the concentration monitoring system according to the embodiment.

The surface treatment line illustrated in FIG. 1 (for example, a surface treatment line of an aircraft member) is an excerpt of a step of performing an anodizing treatment among all steps. A plurality of treatment tanks such as a phosphoric acid treatment tank 2, a primary washing treatment tank 3, and a secondary washing treatment tank 4 are installed in an anodizing treatment line. A crane (not shown) holds a product 5 whose material is made of aluminum, conveys the product 5 to the phosphoric acid treatment tank 2, the primary washing treatment tank 3, and the secondary washing treatment tank 4 in this order, and makes the product 5 to be immersed in treatment liquid of each treatment tank. For example, treatment liquid in which phosphoric acid is diluted is stored in the phosphoric acid treatment tank 2, and the product 5 is immersed in the phosphoric acid treatment tank 2 to perform a film treatment thereon. Thereafter, the product 5 is washed in the primary washing treatment tank 3 and the secondary washing treatment tank 4 in which pure water is stored. By moving the product 5 while being immersed in the treatment liquid of each treatment tank, the anodizing treatment (film treatment) for the product 5 is performed. The concentration monitoring system 1 is connected to the phosphoric acid treatment tank 2. The concentration monitoring system 1 collects the treatment liquid of the phosphoric acid treatment tank 2 and monitors the phosphoric acid concentration of the treatment liquid of the phosphoric acid treatment tank 2.

Figure 2:
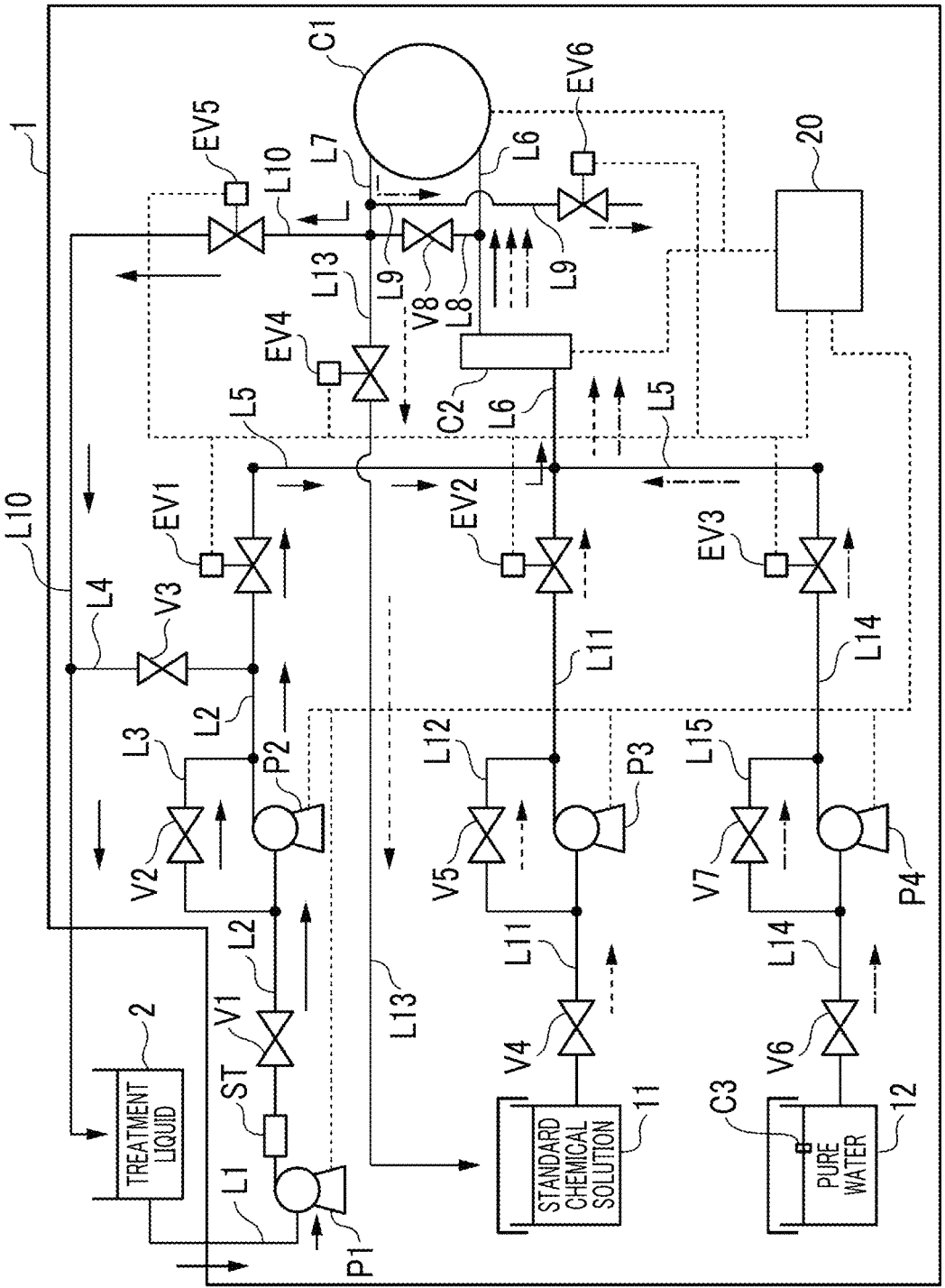
FIG. 2 is a configuration diagram showing an example of the concentration monitoring system according to the embodiment.

FIG. 2 is a configuration diagram showing an example of the concentration monitoring system according to the embodiment.

The concentration monitoring system 1 includes a first cycle, which is a mechanism for monitoring the concentration of treatment liquid, a second cycle, which is a mechanism for inspecting the measurement accuracy of a concentration meter C1 by using a chemical solution having known concentration, a third cycle, which is a mechanism for inspecting a zero point of the concentration meter C1 by using pure water, and a control device 20 for controlling each cycle.

The first cycle is configured to include a strainer ST, pumps P1 to P2, manual valves V1 to V3 and V8, electromagnetic valves EV1 and EV5, the concentration meter C1, a flow meter C2, and pipes L1, L2, L3, L4, L5, L6, L7, L8, and L10 for connecting therebetween.

The second cycle is configured to include a standard chemical solution tank 11, a pump P3, manual valves V4 to V5 and V8, electromagnetic valves EV2 and EV4, the concentration meter C1, the flow meter C2, and pipes L11, L12, L6, L7, L8, and L13 for connecting therebetween.

The third cycle is configured to include a pure water tank 12, a pump P4, manual valves V6 to V7 and V8, electromagnetic valves EV3 and EV6, the concentration meter C1, the flow meter C2, and pipes L14, L15, L5, L6, L7, L8, L9 for connecting therebetween.

The control device 20 is connected to the pumps P1 to P4 and controls the operation of the pumps P1 to P4. The control device 20 is connected to the electromagnetic valves EV1 to EV6 and controls the opening degree of the electromagnetic valves EV1 to EV6. The control device 20 is connected to the concentration meter C1 and the flow meter C2, and acquires values measured by each sensor. The control device 20 is connected to notification means such as a monitor, a lamp, and a buzzer and notifies a monitoring person of the occurrence of an abnormality through the notification means when there is the abnormality in the phosphoric acid concentration of the treatment liquid in the phosphoric acid treatment tank 2.
(First Cycle)

The pump P1 is a circulation pump that draws a sample of the treatment liquid from the phosphoric acid treatment tank 2 into the concentration monitoring system 1 through the pipe L1 connected to the phosphoric acid treatment tank 2. The treatment liquid sucked by the pump P1 is sent to the pipe L2 connected to an outlet side of the pump P1. The pipe L2 is provided with the strainer ST, the manual valve V1, the pump P2, and the electromagnetic valve EV1. The manual valve V1 is normally in an open state, and the sample of the treatment liquid sucked by the pump P1 is filtered by the strainer ST and supplied to the pump P2 through the pipe L2. The pipe L3 that bypasses the pump P2 is connected to the pipe L2, and a manual valve V2 is provided on the pipe L3. The manual valve V2 is a valve for adjusting the flow rate of the sample of the treatment liquid flowing through the pump P2. The manual valve V2 is normally set to a predetermined opening degree. The pipe L4, which guides the sample of the treatment liquid to the pipe L10 in which the sample of the treatment liquid is recirculated to the phosphoric acid treatment tank 2, is connected to the outlet side of the pump P2 of the pipe L2, and the pipe L4 is provided with the manual valve V3. For example, when the maintenance of the concentration monitoring system 1 or the like is performed, by temporarily opening the manual valve V3, the sample of the treatment liquid can be recirculated to the phosphoric acid treatment tank 2 without flowing to the concentration meter C1. The electromagnetic valve EV1 is a valve that adjusts the flow rate of the sample of the treatment liquid supplied to the concentration meter C1. The pipe L2 is connected to the pipe L5, and the pipe L5 is connected to the pipe L6. A flow meter C2 is provided on the pipe L6, and the pipe L6 is connected to the concentration meter C1. The sample of the treatment liquid, which passes through the electromagnetic valve EV1 of the pipe L2, is supplied to the concentration meter C1 by passing through the pipes L5 and L6, the flow meter C2, and the pipe L6. The concentration meter C1 measures the phosphoric acid concentration of the supplied sample of the treatment liquid. The pipe L7 is connected to the outlet side of the concentration meter C1, and the pipe L7 is connected to the pipes L8, L9, L10, and L13. The sample of the treatment liquid after being measured flows out from the concentration meter C1, passes through the pipes L7 and L10, and is returned to the original phosphoric acid treatment tank 2. The pipe L10 is provided with the electromagnetic valve EV5 for adjusting the flow rate of the sample of the treatment liquid. The pipe L8 that bypasses the concentration meter C1 is connected to the pipe L6 and the pipe L7. The pipe L8 is provided with a manual valve V8. The manual valve V8 is a valve for adjusting the flow rate of the sample of the treatment liquid or the like flowing through the concentration meter C1.

The control device 20 operates the pumps P1 and P2 and stops the pumps P3 and P4 while the monitoring of the phosphoric acid concentration of the sample of the treatment liquid that is collected from the phosphoric acid treatment tank 2. The control device 20 adjusts the opening degrees of the electromagnetic valves EV1 and EV5 such that the flow rate of the treatment liquid measured by using the flow meter C2 is within a predetermined range. The control device 20 controls the electromagnetic valves EV2, EV3, EV4, and EV6 to be closed. A solid arrow in FIG. 2 indicates the flow of the sample of the treatment liquid when the first cycle is operated and the concentration monitoring of the phosphoric acid treatment tank 2 is performed.

The concentration meter C1 measures the phosphoric acid concentration of the treatment liquid supplied from the phosphoric acid treatment tank 2 by the first cycle. The concentration meter C1 transmits the measured concentration to the control device 20. The control device 20 compares the phosphoric acid concentration measured by the concentration meter C1 with a predetermined set value and determines whether or not the difference between the two is within an allowable range. When the difference between the measured phosphoric acid concentration and the set value exceeds the allowable range, a phosphoric acid replenishment command or the like is notified by the control device 20.

The concentration monitoring system 1 has a mechanism (second and third cycles) for inspecting the accuracy of the concentration meter C1 in addition to a mechanism for measuring the concentration of the treatment liquid in the phosphoric acid treatment tank 2. For example, the concentration monitoring system 1 supplies a chemical solution or the pure water having the known phosphoric acid concentration to the concentration meter C1 and inspects the measurement accuracy of the concentration meter C1 based on measured values of the concentration meter C1 when those liquids are supplied. Next, these mechanisms will be described.

(Second Cycle)

The phosphoric acid chemical solution having the known concentration is stored in the standard chemical solution tank 11. The pipe L11 for supplying the chemical solution to the concentration meter C1 is connected to the standard chemical solution tank 11. The pipe L11 is provided with the manual valve V4, the pump P3 for sucking the standard chemical solution, and the electromagnetic valve EV2 for regulating the flow rate of the standard chemical solution that is supplied to the concentration meter C1. The pipe L12 that bypasses the pump P3 is connected to the pipe L11. The pipe L12 is provided with the manual valve V5 for adjusting the flow rate of the standard chemical solution flowing through the pump P3. The manual valve V4 and the manual valve V5 are set to a predetermined opening degree. The pipe L11 is connected to the pipe L6. The standard chemical solution that passes through the electromagnetic valve EV2 of the pipe L11 is supplied to the concentration meter C1 by passing through the pipe L6, the flow meter C2, and the pipe L6. The concentration meter C1 measures the phosphoric acid concentration of the supplied standard chemical solution. The standard chemical solution after being measured flows out from the concentration meter C1, passes through the pipes L7 and L13, and is returned to the original standard chemical solution tank 11. The pipe L13 is provided with the electromagnetic valve EV4 for adjusting the flow rate of the standard chemical solution. When the accuracy inspection of the concentration meter C1 by using the standard chemical solution is performed, the control device 20 stops the pumps P1, P2, and P4, and operates the pump P3. The control device 20 adjusts the opening degrees of the electromagnetic valves EV2 and EV4 such that the flow rate of the standard chemical solution measured by the flow meter C2 becomes the predetermined set value and closes the electromagnetic valves EV1, EV3, EV5, and EV6. The flow of the standard chemical solution is indicated by the dashed arrow.

The concentration meter C1 measures the phosphoric acid concentration of the standard chemical solution supplied from the standard chemical solution tank 11 by the second cycle. The concentration meter C1 transmits the measured concentration to the control device 20. The control device 20 compares the phosphoric acid concentration, which is measured by using the concentration meter C1, with the known phosphoric acid concentration of the standard chemical solution and determines whether or not a difference thereof is within the predetermined allowable range. When the difference between the two is not within the allowable range, the fact that there is a suspected failure in the concentration meter C1 is notified by the control device 20.

(Third Cycle)

The pure water is stored in the pure water tank 12. The pipe L14 for supplying the pure water to the concentration meter C1 is connected to the pure water tank 12. The pipe L14 is provided with the manual valve V6, the pump P4 for sucking the pure water, and the electromagnetic valve EV3 for regulating the flow rate of the pure water supplied to the concentration meter C1. The pipe L15 that bypasses the pump P4 is connected to the pipe L14, and the manual valve V7 for adjusting the flow rate of the pure water flowing through the pump P4 is provided on the pipe L15. The manual valve V6 and the manual valve V7 are set to a predetermined opening degree. The pipe L14 is connected to the pipe L5. The pure water that passes through the electromagnetic valve EV3 of the pipe L14 is supplied to the concentration meter C1 by passing through the pipes L5 and L6, the flow meter C2, and the pipe L6. The concentration meter C1 measures the concentration of the phosphoric acid in the supplied pure water. The pure water after being measured flows out from the concentration meter C1, passes through the pipes L7 and L9, and is discarded. The pipe L9 is provided with the electromagnetic valve EV6 for adjusting the flow rate of the pure water to be discarded. The pure water tank 12 is provided with a flow sensor C3 that detects the amount of the stored pure water. When the amount of the pure water is lowered than a predetermined value, the pure water is supplied to the pure water tank 12 from a pure water tank (not shown). When the accuracy inspection (zero point inspection) of the concentration meter C1 by using the pure water is performed, the control device 20 stops the pumps P1, P2, and P3 and operates the pump P4. The control device 20 adjusts the opening degrees of the electromagnetic valves EV3 and EV6 such that the flow rate of the pure water measured by the flow meter C2 becomes a predetermined set value. The control device 20 controls the electromagnetic valves EV1, EV2, EV4, and EV5 to be closed. The flow of the pure water is indicated by the alternate long and short dash arrow.

The concentration meter C1 measures the phosphoric acid concentration of the pure water supplied from the pure water tank 12 by the third cycle. The concentration meter C1 transmits the measured concentration to the control device 20. The control device 20 compares the phosphoric acid concentration measured by the concentration meter C1 with zero and determines whether or not a difference therebetween is within the predetermined allowable range. When the measured phosphoric acid concentration deviates significantly from zero, the fact that there is a suspected failure in the concentration meter C1 is notified by the control device 20.

In the concentration monitoring system 1, the concentration monitoring of the phosphoric acid treatment tank 2 is consecutively and continuously performed by the first cycle at predetermined time intervals (for example, every few minutes), and the accuracy inspection of the concentration meter C1 is intermittently (for example, every day) performed by the second cycle or the third cycle. By controlling the control device 20 as described above, it is possible to smoothly switch between the concentration monitoring of the phosphoric acid treatment tank 2 and the accuracy inspection of the concentration meter. Therefore, it is possible to maintain the accuracy of the concentration monitoring by performing the accuracy inspection of the concentration meter C1 without interfering with the concentration monitoring of the phosphoric acid treatment tank 2. When the measurement accuracy of the concentration meter C1 is lowered, it is possible to resume the accurate concentration monitoring by promptly performing the maintenance, exchange, or the like of the concentration meter C1.

Figure 3:
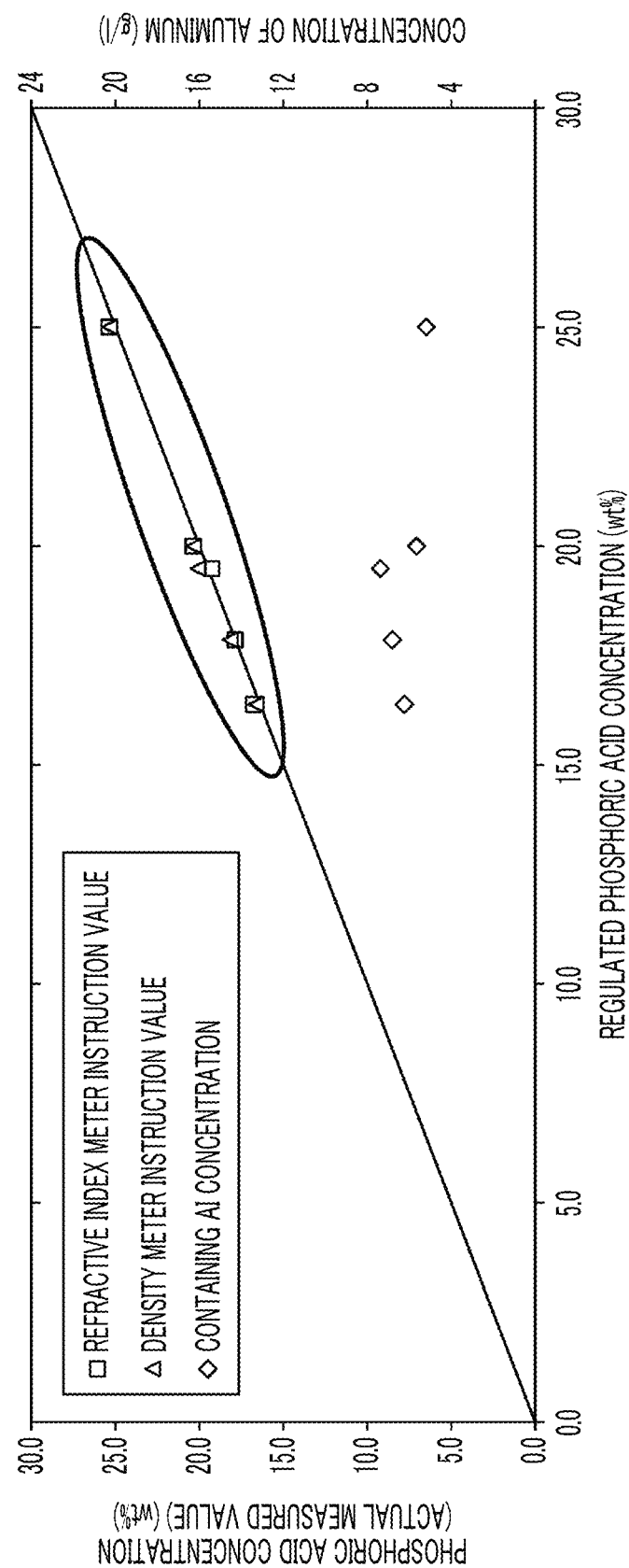
FIG. 3 is a diagram describing a concentration meter according to the embodiment.

The concentration meter C1 of the present embodiment is a density/sound velocity combined sensor. The measurement performance of the concentration meter C1 is shown in FIG. 3. FIG. 3 is a diagram describing the concentration meter according to the embodiment.

The vertical axis in FIG. 3 is the measured value of the phosphoric acid concentration of the test treatment liquid measured by using the concentration meter C1, and the horizontal axis is the phosphoric acid concentration of the test treatment liquid. The phosphoric acid concentration of the test treatment liquid is known.

In the figure, a diamond-shaped dot indicates the concentration of aluminum in the test treatment liquid measured by the sound velocity sensor of the density/sound velocity combined sensor. The sound velocity sensor measures the concentration of the aluminum by utilizing the property that the sound velocity changes due to the concentration. By using the density/sound velocity combined sensor, it is possible to measure the concentration of the aluminum dissolved in the treatment liquid. In the figure, a triangular dot indicates a value obtained by correcting the phosphoric acid concentration of the test treatment liquid measured by the density sensor of the density/sound velocity combined sensor with the concentration of the aluminum by the sound velocity sensor. As indicated by the triangular dot, the density/sound velocity combined sensor can accurately measure the phosphoric acid concentration.

A square dot indicates the measurement result by a refractive index meter that measures the phosphoric acid concentration by using the refractive index. The phosphoric acid concentration can also be measured accurately by using the refractive index meter.

(Operation)

Next, the monitoring process of the treatment liquid in the phosphoric acid treatment tank 2 by the concentration monitoring system 1 will be described with reference to FIG. 4.

Figure 4:
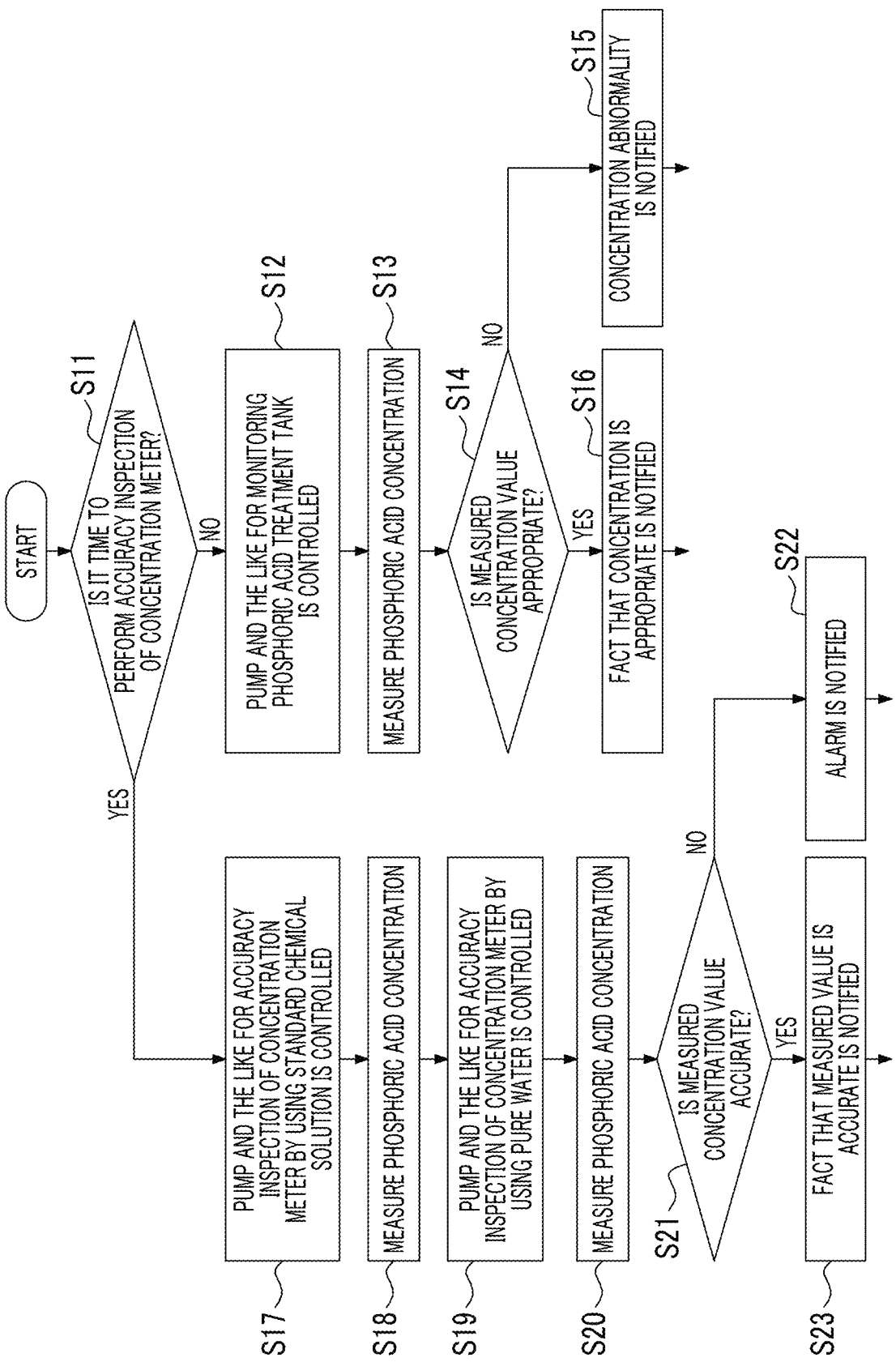
FIG. 4 is a flowchart showing an example of a concentration monitoring process according to the embodiment.

FIG. 4 is a flowchart showing an example of the concentration monitoring process according to the embodiment.

As a premise, it is assumed that the control device 20 stores in advance each information such as time to perform the accuracy inspection of the concentration meter C1 (for example, once a day), a time zone for monitoring the phosphoric acid treatment tank 2 (for example, time zone excluding the time for performing the accuracy inspection), the allowable range of the phosphoric acid concentration in the treatment liquid of the phosphoric acid treatment tank 2, the phosphoric acid concentration of the standard chemical solution, and the set value of the flow rate measured by the flow meter C2. The control device 20 performs the following processes in a predetermined control cycle while the concentration monitoring system 1 is in operation.

First, the control device 20 determines whether or not it is the time to perform the accuracy inspection of the concentration meter C1 (step S11). For example, when the current time is included in the time for performing the accuracy inspection of the concentration meter C1, the control device 20 determines to perform the accuracy inspection.

When it is determined that the accuracy inspection is to be performed (step S11: Yes), the control device 20 controls the pump P1 and the like for the accuracy inspection of the concentration meter C1 by using the standard chemical solution (step S17). Specifically, the control device 20 operates the pump P3 and stops the other pumps P1 and the like. The control device 20 opens the electromagnetic valves EV2 and EV4 at the appropriate opening degree and closes the other electromagnetic valve EV1 and the like while referring to the flow rate measured by the flow meter C2. As a result, the standard chemical solution is supplied from the standard chemical solution tank 11 to the concentration meter C1. The concentration meter C1 measures the phosphoric acid concentration of the standard chemical solution (step S18). The concentration meter C1 outputs the measured value of the phosphoric acid concentration to the control device 20. The control device acquires the measured value of the phosphoric acid concentration and temporarily stores the measured value.

Next, the control device 20 controls the pump P1 and the like for the accuracy inspection of the concentration meter C1 by using the pure water (step S19). Specifically, the control device 20 operates the pump P4 and stops the other pumps P1 and the like. The control device 20 opens the electromagnetic valves EV3 and EV6 at the appropriate opening degree and closes the other electromagnetic valve EV1 and the like while referring to the flow rate measured by the flow meter C2. As a result, the pure water is supplied from the pure water tank 12 to the concentration meter C1. The concentration meter C1 measures the phosphoric acid concentration of the pure water (step S20). The concentration meter C1 outputs the measured value of the phosphoric acid concentration to the control device 20. The control device 20 acquires the measured value of the phosphoric acid concentration and temporarily stores the measured value.

Next, the control device 20 determines whether or not the measured concentration values measured in steps S18 and S20 are accurate (step S21). Specifically, the control device 20 determines that the measured value of the concentration meter C1 is accurate when a difference between the phosphoric acid concentration measured in step S18 and the concentration of the standard chemical solution is within the predetermined allowable range, and determines that the measured value of the concentration meter C1 is not accurate when the difference is out of the allowable range. The control device 20 determines that the measured value of the concentration meter C1 is accurate when a difference between the phosphoric acid concentration measured in step S20 and the phosphoric acid concentration of the pure water (concentration zero) is within the predetermined allowable range, and determines that the measured value of the concentration meter C1 is not accurate when the difference is out of the allowable range. The control device 20 may determine that the measured value of the concentration meter C1 is not accurate when any of the difference between the phosphoric acid concentration measured in steps S18 and S20 and the each of the set values is out of the predetermined allowable range. Alternatively, the control device 20 may determine that the measured value of the concentration meter C1 is not accurate when both differences between the phosphoric acid concentration measured in steps S18 and S20 and the each of the set values are out of the predetermined allowable range. When it is determined that the measured value of the concentration meter C1 is not accurate (step S21: No), an alarm that there is a possibility that the concentration meter C1 has a failure is notified by the control device 20 (step S22). For example, the control device 20 may display the alarm on a monitor together with the measured concentration value. When it is determined that the measured concentration value is accurate (step S21: Yes), the fact that the measured value of the concentration meter C1 is accurate is notified by the control device 20 (step S23).

Regardless of the determination result in step S20, the control device 20 repeats the processes from step S11.

When the accuracy inspection of the concentration meter C1 is performed, it is assumed that the accuracy inspection by using the standard chemical solution and the accuracy inspection by using the pure water are continuously performed, but the time for performing the accuracy inspection by using the standard chemical solution and the time for performing the accuracy inspection by using the pure water may be staggered and performed independently.

On the other hand, when it is determined that the accuracy inspection is not performed in step S11 (step S11: No), the control device 20 controls the pump P1 and the like for monitoring the phosphoric acid concentration in the phosphoric acid treatment tank 2 (step S12). Specifically, the control device 20 operates the pumps P1 and P2 and stops the other pumps P3 and P4. The control device 20 opens the electromagnetic valves EV1 and EV5 at the appropriate opening degree and closes the other electromagnetic valve EV2 and the like while referring to the flow rate measured by the flow meter C2. As a result, the sample of the treatment liquid collected from the phosphoric acid treatment tank 2 is supplied to the concentration meter C1. The concentration meter C1 measures the phosphoric acid concentration of the sample of the treatment liquid (step S13). The concentration meter C1 outputs the measured value of the phosphoric acid concentration to the control device 20. The control device 20 acquires the measured value of the phosphoric acid concentration and temporarily stores the measured value.

Next, the control device 20 determines whether or not the measured concentration value measured in step S13 is appropriate (step S14). Specifically, the control device 20 determines that the phosphoric acid concentration in the phosphoric acid treatment tank 2 is appropriate when a difference between the phosphoric acid concentration measured in step S13 and the set value of the phosphoric acid concentration in the phosphoric acid treatment tank 2 is within the predetermined allowable range. When it is determined that the phosphoric acid concentration is appropriate (step S14: Yes), the fact that the phosphoric acid concentration in the phosphoric acid treatment tank 2 is appropriate is notified by the control device 20 (step S16). When it is determined that the phosphoric acid concentration is not appropriate (step S14: No), the fact that the phosphoric acid concentration in the phosphoric acid treatment tank 2 is abnormal is notified by the control device 20 (step S15). For example, the control device 20 may display an instruction to add phosphoric acid or a diluted solution on the monitor together with the measured concentration value.

Regardless of the determination result in step S14, the control device 20 repeats the processes from step S11.

The concentration monitoring system 1 of the present embodiment includes the first cycle for supplying the sample of the treatment liquid in the phosphoric acid treatment tank 2 to the concentration meter C1, the second cycle for supplying the standard chemical solution (liquid having the known phosphoric acid concentration) to the concentration meter C1, and the third cycle for supplying the pure water (phosphoric acid concentration zero) to the concentration meter C1. Thereafter, normally, the first cycle is operated to consecutively perform the concentration monitoring of the phosphoric acid treatment tank 2. The second cycle and the third cycle are intermittently operated to inspect the measurement accuracy of the concentration meter C1. According to the present embodiment, it is possible to continuously perform the concentration monitoring in which the measurement accuracy of the phosphoric acid concentration is guaranteed. As a result, even when the change is occurred in the phosphoric acid concentration in the phosphoric acid treatment tank 2 due to a variation in the number of productions of the product 5, the change can be quickly detected and handled. Therefore, the quality of the product 5 in the surface treatment line can be ensured, and the occurrence of yield can be reduced.

Although FIG. 2 shows a configuration example of the concentration monitoring system 1 in which both the second cycle and the third cycle mechanisms are provided, a configuration in which only one is provided may be used. A refractive index meter may be used for the concentration meter C1 instead of the density/sound velocity combined sensor.

(Configuration of Concentration Management System)

Next, a concentration management system 100 capable of automatically adding a chemical or a diluted solution to the phosphoric acid treatment tank 2 to maintain a normal concentration in response to a concentration abnormality in the phosphoric acid treatment tank 2 detected by the concentration monitoring system 1, will be described.

Figure 5:
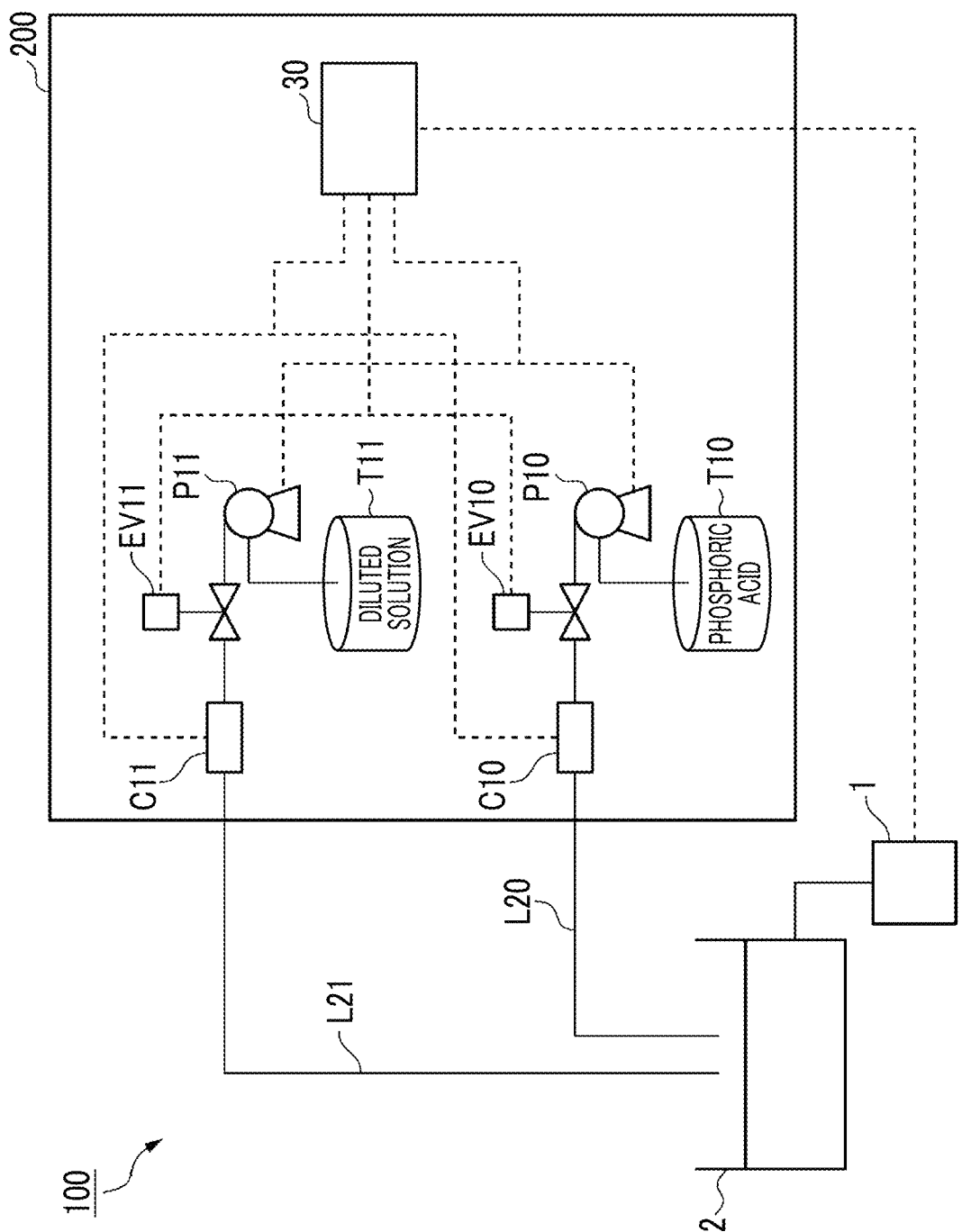
FIG. 5 is a configuration diagram showing an example of a concentration management system according to the embodiment.

FIG. 5 is a configuration diagram showing an example of the concentration management system according to the embodiment.

The concentration management system 100 includes the phosphoric acid treatment tank 2, the concentration monitoring system 1, and an automatic addition system 200. The automatic addition system 200 includes a phosphoric acid tank T10, a pump P10, an electromagnetic valve EV10, a flow meter C10, a diluted solution tank T11, a pump P11, an electromagnetic valve EV11, a flow meter C11, and a control device 30.

The phosphoric acid tank T10, the pump P10, the electromagnetic valve EV10, and the flow meter C10 are connected by a pipe L20, and this pipe L20 is connected to the phosphoric acid treatment tank 2. The diluted solution tank T11, the pump P11, the electromagnetic valve EV11, and the flow meter C11 are connected by a pipe L21, and the pipe L21 is connected to the phosphoric acid treatment tank 2.

The control device 30 is connected to the concentration monitoring system 1, the pumps P10 and P11, the electromagnetic valves EV10 and EV11, and the flow meters C10 and C11. The control device 30 acquires a notification of a concentration abnormality in the phosphoric acid treatment tank 2 from the concentration monitoring system 1. The control device 30 acquires the measured value of the flow rate measured by using the flow meters C10 and C11. The control device 30 controls the operation of the pumps P10 and P11 and the opening degrees of the electromagnetic valves EV10 and EV11.

(Operation)

In the normal time, the control device 30 stops the pumps P10 and P11. In the surface treatment line illustrated in FIG. 1, the product 5 is conveyed to each of the treatment tanks 2 to 4, and the anodizing treatment is performed. The concentration monitoring system 1 monitors the phosphoric acid concentration in the phosphoric acid treatment tank 2. When the abnormality in the phosphoric acid concentration is detected (No in step S14 in FIG. 4), the control device 20 notifies the control device 30 of the concentration abnormality. For example, the control device 20 notifies the control device 30 of the phosphoric acid concentration in the sample of the treatment liquid. Thereafter, the control device 30 determines whether the phosphoric acid concentration in the phosphoric acid treatment tank 2 is high or low based on the phosphoric acid concentration of the sample of the treatment liquid acquired from the control device 20 and the predetermined set value. When it is determined that the phosphoric acid concentration is high, the control device 30 calculates the amount of the diluted solution required to return the phosphoric acid concentration to the set value based on a predetermined calculation equation or a trained model. The control device 30 supplies the calculated amount of the diluted solution to the phosphoric acid treatment tank 2. For example, the control device 30 activates the pump P11 and sucks the diluted solution from the diluted solution tank T11. The control device 30 adjusts the opening degree of the electromagnetic valve EV11 with reference to the measured value of the flow meter C11 and supplies the calculated amount of the diluted solution to the phosphoric acid treatment tank 2. In contrast to this, when it is determined that the phosphoric acid concentration is low, the control device 30 calculates the amount of phosphoric acid required to return the phosphoric acid concentration to the set value based on the predetermined calculation equation or the trained model. The control device 30 supplies the calculated amount of phosphoric acid to the phosphoric acid treatment tank 2. For example, the control device 30 activates the pump P10 and sucks the phosphoric acid from the phosphoric acid tank T10. The control device 30 adjusts the opening degree of the electromagnetic valve EV10 with reference to the measured value of the flow meter C10 and supplies the calculated amount of the diluted solution to the phosphoric acid treatment tank 2. During the addition of the diluted solution or the phosphoric acid, the concentration monitoring system 1 monitors the phosphoric acid concentration in the phosphoric acid treatment tank 2 and transmits the measured concentration to the control device 30. The control device 30 consecutively supplies the diluted solution or the phosphoric acid until the phosphoric acid concentration in the phosphoric acid treatment tank 2 is set to the set value.

According to the concentration management system 100 of the present embodiment, the phosphoric acid concentration in the phosphoric acid treatment tank 2 can be automatically maintained at a predetermined concentration.

Figure 6:
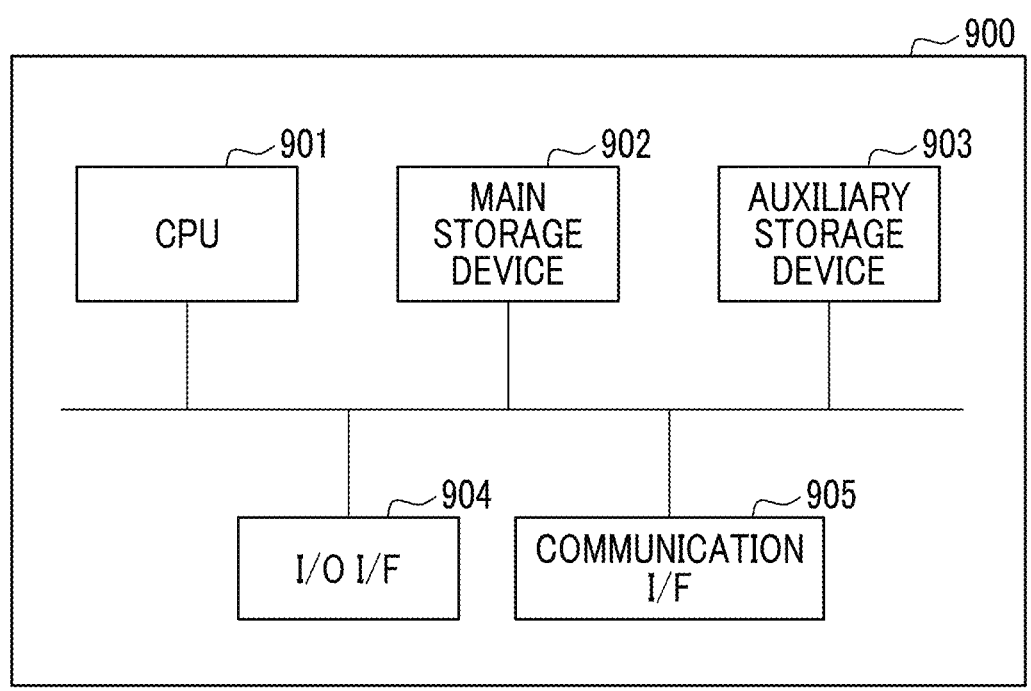
FIG. 6 is a diagram showing an example of a hardware configuration of a control device according to the embodiment.

FIG. 6 is a diagram showing an example of a hardware configuration of the control device according to the embodiment.

A computer 900 includes a CPU 901, a main storage device 902, an auxiliary storage device 903, an I/O interface 904, and a communication interface 905.

The control devices 20 and 30 described above are mounted on the computer 900. Further, the above-mentioned each function is stored in the auxiliary storage device 903 in the form of a program. The CPU 901 reads the program from the auxiliary storage device 903, loads the program into the main storage device 902, and executes the above treatments according to the program. The CPU 901 ensures a storage area in the main storage device 902 according to the program. The CPU 901 ensures a storage area for storing the data being processed in the auxiliary storage device 903 according to the program.

A program for implementing all or a part of the functions of the control devices 20 and 30 may be recorded on a computer-readable recording medium, and the program recorded on the recording medium may be read by a computer system and executed to perform processes by each functional unit. The term "computer system" as used herein includes hardware such as an OS or peripheral devices. The "computer system" is also assumed to include a homepage providing environment (or display environment) when a WWW system is used. The "computer-readable recording medium" refers to a portable medium such as a CD, DVD, or USB, or a storage device such as a hard disk built in the computer system. When this program is distributed to the computer 900 by using a communication line, the computer 900, which is received the distribution of the program, may load the program into the main storage device 902 and execute the above processes. The above-mentioned program may be a program for implementing a part of the above-mentioned functions and further implementing the above-mentioned functions in combination with a program already recorded in the computer system.

The control devices 20 and 30 may be constituted by a plurality of computers 900 capable of communicating with each other.

As described above, some embodiments according to the present disclosure have been described, but all of these embodiments are presented as examples and are not intended to limit the scope of the invention. These embodiments can be implemented in various other forms, and various omissions, replacements, and changes can be made without departing from the gist of the invention. These embodiments and variations thereof are included in the scope of the invention described in the claims and the equivalent scope thereof, as are included in the scope and gist of the invention.

<Additional Notes>

The concentration monitoring system 1, the concentration management system 100, and the concentration monitoring method described in each embodiment are ascertained as follows, for example.

(1) According to a first aspect, there is provided a concentration monitoring system 1 including: a first cycle for collecting a sample of treatment liquid from a treatment tank (phosphoric acid treatment tank 2), which stores the treatment liquid to which a chemical (phosphoric acid) is added, and supplying the sample to a concentration meter C1 which measures concentration of the chemical; a second cycle for supplying a chemical solution (standard chemical solution) having known concentration of the chemical to the concentration meter C1; and a control device 20 that controls the first cycle to evaluate concentration of the chemical in the treatment tank based on concentration of the sample measured by using the concentration meter C1, and controls the second cycle to evaluate accuracy of the concentration meter C1 based on concentration of the chemical solution measured by using the concentration meter.

According to the concentration monitoring system 1, the sample of the treatment liquid is collected in the first cycle and supplied to the concentration meter C1, and the concentration that is measured by using the concentration meter C1 is determined, thereby it is possible to monitor whether the concentration in the treatment tank is appropriate. By continuously supplying the sample to the concentration meter C1 in the first cycle, it is possible to perform the continuous and consecutive concentration monitoring.

According to the concentration monitoring system 1, the chemical solution having the known concentration is supplied to the concentration meter C1 in the second cycle, and the concentration measured by the concentration meter C1 is compared with the known concentration, thereby it is possible to inspect the measurement accuracy of the concentration meter C1. By performing the accuracy inspection of the concentration meter C1, the accuracy of the concentration monitoring can be ensured.

(2) The concentration monitoring system 1 according to a second aspect is the concentration monitoring system 1 of (1), in which the control device 20 operates the first cycle and stops the second cycle to monitor the concentration in the treatment tank, and intermittently stops the first cycle and operates the second cycle while the first cycle is intermittently stopped to perform an accuracy inspection of the concentration meter.

As a result, the concentration monitoring of the treatment liquid in the phosphoric acid treatment tank 2 can be continuously performed, and the accuracy inspection of the concentration meter C1 can be performed between the concentration monitoring. The accuracy inspection of the concentration meter C1 can be performed without being affected by the concentration of the treatment liquid in the phosphoric acid treatment tank 2. The concentration monitoring of the treatment liquid in the phosphoric acid treatment tank 2 can be performed without being affected by the chemical solution having the known concentration.

(3) The concentration monitoring system 1 according to a third aspect is the concentration monitoring system 1 of (1) or (2), a third cycle for supplying pure water to the concentration meter is further included, in which the control device 20 evaluates the accuracy of the concentration meter C1 based on concentration of the chemical in the pure water measured by the concentration meter C1.

By performing the accuracy inspection of the concentration meter C1 by using the pure water in which the chemical is not included, it is possible to evaluate whether or not the zero point of the concentration meter C1 is correct.

(4) According to a fourth aspect, there is provided a concentration monitoring system 1 including: a first cycle for collecting a sample of treatment liquid from a treatment tank (phosphoric acid treatment tank 2), which stores the treatment liquid to which a chemical (phosphoric acid) is added, and supplying the sample to a concentration meter C1 which measures concentration of the chemical; a third cycle for supplying a chemical solution (pure water), in which concentration of the chemical is zero, to the concentration meter C1; and a control device that controls the first cycle to evaluate concentration of the chemical in the treatment tank based on concentration of the sample measured by using the concentration meter C1, and controls the third cycle to inspect a zero point of the concentration meter based on concentration of the chemical solution measured by using the concentration meter C1.

According to the concentration monitoring system 1, the sample of the treatment liquid is collected in the first cycle and supplied to the concentration meter C1, and the concentration that is measured by using the concentration meter C1 is determined, thereby it is possible to monitor whether the concentration in the treatment tank is appropriate. According to the concentration monitoring system 1, the chemical solution in which the concentration of the chemical is zero is supplied to the concentration meter C1 in the third cycle, and the measurement accuracy of the concentration meter C1 can be inspected by evaluating whether or not the zero point of the concentration meter C1 is correct based on the concentration measured by the concentration meter C1. By performing the accuracy inspection of the concentration meter C1, the accuracy of the concentration monitoring can be ensured.

(5) According to a fifth aspect, there is provided a concentration management system 100 including: the concentration monitoring system 1 of any one of (1) to (4); and an automatic addition system 200 that adds the chemical or a diluted solution of the chemical to the treatment tank when the concentration monitoring system 1 evaluates that the concentration in the treatment tank is abnormal.

According to the concentration management system 100, the phosphoric acid concentration in the phosphoric acid treatment tank 2 can be maintained at an appropriate concentration.

(6) According to a sixth aspect, there is provided a concentration monitoring method including: collecting a sample of treatment liquid from a treatment tank (phosphoric acid treatment tank 2), which stores the treatment liquid to which a chemical (phosphoric acid) is added, supplying the sample to a concentration meter C1 which measures concentration of the chemical, and evaluating concentration of the chemical in the treatment tank; and supplying a chemical solution having known concentration of the chemical to the concentration meter C1 while the sample is not supplied to the concentration meter and evaluating accuracy of the concentration meter C1 based on concentration of the chemical solution measured by using the concentration meter C1.

REFERENCE SIGNS LIST

1 concentration monitoring system
2 phosphoric acid treatment tank
3 primary washing treatment tank
4 secondary washing treatment tank
P1 to P4, P10, P11 pump
V1 to V8 manual valve
EV1 to EV6, EV10, EV11 electromagnetic valve
C1 concentration meter
C2, C10, C11 flow meter
C3 flow sensor
11 standard chemical solution tank
12 pure water tank
20, 30 control device
100 concentration management system
200 automatic addition system
900 computer
901 CPU
902 main storage device
903 auxiliary storage device
904 I/O interface
905 communication interface

The invention claimed is:
1. A concentration monitoring system comprising:
 a first cycle mechanism for collecting a sample of treatment liquid from a treatment tank, which stores the treatment liquid to which a chemical is added, and supplying the sample to a concentration meter which measures concentration of the chemical;

a second cycle mechanism for supplying a chemical solution having known concentration of the chemical to the concentration meter; and a control device that is configured to:
control the first cycle mechanism to evaluate concentration of the chemical in the treatment tank based on concentration of the sample measured by using the concentration meter, and
control the second cycle mechanism to evaluate accuracy of the concentration meter based on concentration of the chemical solution measured by using the concentration meter, wherein the first cycle mechanism includes a first pipe connecting the treatment tank and an inlet side of the concentration meter, and a second pipe connecting the treatment tank and an outlet side of the concentration meter, wherein the first pipe is provided with a first pump and a first valve, and the second pipe is provided with a second valve, wherein the second cycle mechanism includes a third pipe connecting a standard chemical solution tank in which a chemical solution having a known concentration is stored and the inlet side of the concentration meter, and a fourth pipe connecting the standard chemical solution tank and the outlet side of the concentration meter, wherein the third pipe is provided with a second pump and a third valve, and the fourth pipe is provided with a fourth valve, wherein, when evaluating the concentration of the chemical in the treatment tank, the control device is configured to open the first valve and the second valve, close the third valve and the fourth valve, activate the first pump, and stop the second pump, wherein, when evaluating the concentration of the chemical in the standard chemical solution tank, the control device is configured to open the third valve and the fourth valve, close the first valve and the second valve, activate the second pump, and stop the first pump, and wherein the concentration meter includes a density/sound velocity combined sensor which measures the concentration of the chemical in the treatment tank, the treatment tank is installed in a surface treatment line and used for a surface treatment, and the first cycle mechanism is configured to guide the sample of the treatment liquid from the concentration meter to return to the treatment tank and to be reused for the surface treatment.

2. The concentration monitoring system according to claim 1, wherein
the control device is configured to
operate the first cycle mechanism and stop the second cycle mechanism to monitor the concentration in the treatment tank, and
intermittently stop the first cycle mechanism and operate the second cycle mechanism while the first cycle mechanism is intermittently stopped to perform an accuracy inspection of the concentration meter.

3. The concentration monitoring system according to claim 1, further comprising:
a third cycle mechanism for supplying pure water to the concentration meter, wherein the control device is configured to evaluate the accuracy of the concentration meter based on concentration of the chemical in the pure water measured by the concentration meter.

4. A concentration monitoring system comprising:
a first cycle mechanism for collecting a sample of treatment liquid from a treatment tank, which stores the treatment liquid to which a chemical is added, and supplying the sample to a concentration meter which measures concentration of the chemical;

a second cycle mechanism for supplying a chemical solution, in which concentration of the chemical is zero, to the concentration meter; and a control device that is configured to:
control the first cycle mechanism to evaluate concentration of the chemical in the treatment tank based on concentration of the sample measured by using the concentration meter, and
control the second cycle mechanism to inspect a zero point of the concentration meter based on concentration of the chemical solution measured by using the concentration meter, wherein the first cycle mechanism includes a first pipe connecting the treatment tank and an inlet side of the concentration meter, and a second pipe connecting the treatment tank and an outlet side of the concentration meter, wherein the first pipe is provided with a first pump and a first valve, and the second pipe is provided with a second valve, wherein the second cycle mechanism includes a third pipe connecting a pure water tank in which a pure water is stored and the inlet side of the concentration meter, and a fourth pipe connecting the pure water tank and the outlet side of the concentration meter, wherein the third pipe is provided with a second pump and a third valve, and the fourth pipe is provided with a fourth valve, wherein, when evaluating the concentration of the chemical in the treatment tank, the control device is configured to open the first valve and the second valve, close the third valve and the fourth valve, activate the first pump, and stop the second pump, wherein, when inspecting the zero point of the concentration meter, the control device is configured to open the third valve and the fourth valve, close the first valve and the second valve, activate the second pump, and stop the first pump, and
wherein
the concentration meter includes a density/sound velocity combined sensor which measures the concentration of the chemical in the treatment tank, the treatment tank is installed in a surface treatment line and used for a surface treatment, and the first cycle mechanism is configured to guide the sample of the treatment liquid from the concentration meter to return to the treatment tank and to be reused for the surface treatment.

5. A concentration management system comprising:
the centration monitoring system according to claim 4; and
an automatic addition system configured to add the chemical or a diluted solution of the chemical to the treatment tank in response to the concentration monitoring system evaluating that the concentration in the treatment tank is abnormal.

6. A concentration management system comprising:
the centration monitoring system according to claim 1; and an automatic addition system configured to add the chemical or a diluted solution of the chemical to the treatment tank in response to the concentration monitoring system evaluating that the concentration in the treatment tank is abnormal.

7. A concentration monitoring method for a concentration monitoring system which includes a first cycle mechanism and a second cycle mechanism, wherein the first cycle mechanism includes a first pipe connecting a treatment tank to an inlet side of a concentration meter, wherein the treatment tank stores a treatment liquid to which a chemical is added, and a second pipe connecting the treatment tank and an outlet side of the concentration meter, wherein the first pipe is provided with a first pump and a first valve, and the second pipe is provided with a second valve, and wherein the second cycle mechanism includes a third pipe connecting a standard chemical solution tank in which a chemical solution having a known concentration is stored and the inlet side of the concentration meter, and a fourth pipe connecting the standard chemical solution tank and the outlet side of the concentration meter, wherein the third pipe is provided with a second pump and a third valve, and the fourth pipe is provided with a fourth valve, the method comprising:

opening the first valve and the second valve, closing the third valve and the fourth valve, activating the first pump, stopping the second pump, collecting a sample of the treatment liquid from the treatment tank, supplying the sample to the concentration meter which measures concentration of the chemical, and evaluating concentration of the chemical in the treatment tank; and opening the third valve and the fourth valve, closing the first valve and the second valve, activating the second pump, stopping the first pump, supplying a chemical solution having known concentration of the chemical to the concentration meter while the sample is not supplied to the concentration meter and evaluating accuracy of the concentration meter based on concentration of the chemical solution measured by using the concentration meter, wherein the concentration meter includes a density/sound velocity combined sensor which measures the concentration of the chemical in the treatment tank, the treatment tank is installed in a surface treatment line and used for a surface treatment, and the first cycle mechanism guides the sample of the treatment liquid from the concentration meter to return to the treatment tank and to be reused for the surface treatment.

* * * * *